United States Patent [19]

Wang et al.

[11] 4,375,548

[45] Mar. 1, 1983

[54] PREPARATION OF TRICHLOROMETHYL CARBINOLS

[75] Inventors: Pen-Chung Wang; James M. Renga, both of Midland, Mich.

[73] Assignee: The Dow Chemical Company, Midland, Mich.

[21] Appl. No.: 331,854

[22] Filed: Dec. 17, 1981

[51] Int. Cl.$^3$ ............................ C07F 7/18; C07F 7/04
[52] U.S. Cl. ..................................... 556/470; 568/812; 556/438; 556/440; 556/449; 556/436; 556/445
[58] Field of Search ............... 556/470, 438, 440, 449, 556/445, 436

[56] References Cited

U.S. PATENT DOCUMENTS 3,472,888 10/1969 Bazouin et al. ...................... 556/470
3,536,745 10/1970 Dear .................................... 556/470

FOREIGN PATENT DOCUMENTS 1227022 1/1965 Fed. Rep. of Germany ...... 556/470

OTHER PUBLICATIONS

W. Reeve, *Synthesis*, (Mar. 1971), pp. 131–138.

*Primary Examiner*—Paul F. Shaver
*Attorney, Agent, or Firm*—Douglas N. Deline

[57] ABSTRACT

Silylated trichloromethyl carbinol compounds are prepared by contacting aldehydes and ketones with silylated trichloroacetates at elevated temperatures in the presence of an initiator.

9 Claims, No Drawings

PREPARATION OF TRICHLOROMETHYL CARBINOLS

BACKGROUND OF THE INVENTION

The invention relates to a new chemical process and more particularly to a novel process which allows the preparation of organic compounds having both trichloromethyl and organosiloxy functionality. The products may be converted to the corresponding trichloromethyl-substituted hydroxyl-containing compounds which are useful as intermediates for the selective preparation of α-substituted acid chlorides. Thus, the process provides a unique and utile method for preparing reactive carbinol precursors having protected hydroxyl functionality.

W. Reeve, in *Synthesis*, 131 (1971) disclosed applications adapted to the use of trichloromethyl carbinol compounds. In particular, the reference described a wide variety of reactions between trichloromethyl carbinols and reactive nucleophiles to prepare α-substituted acid chlorides, amino acids and mercapto acids.

Previously known techniques for the preparation of aryl-(trichloromethyl) carbinols include the reaction of aromatic hydrocarbons with chloral in the presence of a Lewis acid or the reaction of arylmagnesium bromide with chloral.

It is also known to prepare aryl-(trichloromethyl) carbinols and alkyl-(trichloromethyl) carbinols by the reaction of carbonyl compounds with chloroform in the presence of caustic and a phase-transfer catalyst such as a quaternary ammonium salt.

Additional processes include electrochemical reduction of carbon tetrachloride and subsequent reaction of the carbon trichloride anions with electrophilic aldehydes. In the presence of hydrogen-containing solvents, e.g., chloroform, the intermediate reaction product abstracts a proton from the solvent thereby preparing the desired trichloromethyl-substituted carbinol compound.

SUMMARY OF THE INVENTION

According to the present invention is provided a novel process comprising the reaction of aliphatic or aromatic aldehydes or ketones with silylated trichloroacetates.

By means of the invented process the aldehyde or ketone is easily converted to the corresponding siloxated trichloromethyl functionalized compounds. Under mildly acidic conditions, these compounds are readily desilylated to produce the corresponding trichloromethyl carbinol.

DETAILED DESCRIPTION OF THE INVENTION

Aldehydes and ketones suitably employed in the instant process include those compounds corresponding to the formula

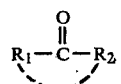

wherein $R_1$ and $R_2$ individually are hydrogen or a hydrocarbyl radical of up to about 20 carbons selected from the group consisting of alkyl, alkenyl, aryl, and inertly-substituted derivatives thereof, provided that at least one of $R_1$ or $R_2$ is a hydrocarbyl radical; or $R_1$ and $R_2$ collectively form a hydrocarbylene moiety of up to about 20 carbons selected from the group consisting of alkylene, alkenylene and inertly functionalized derivatives thereof.

By inert functionality or inertly functionalized is meant that the additional functionality does not interfere with the desired chemical reaction. It is possible, however, that the added functionality may also react with the silylated trichloroacetate reactant. For example, it is known that reactive hydrogen moieties, e.g., hydroxyl or carboxylic acid moieties will also react with the silylated trichloroacetate reactant thereby producing siloxane functionality while simultaneously decomposing the silylated trichloroacetate reactant to carbon dioxide and chloroform. However, the presence of such functionality does not interfere with the desired reaction at the carbonyl site of the aldehyde or ketone.

Examples of inert functionality that may be present in the aldehyde or ketone reactant include alkyl, aryl, alkoxy, polyalkoxy, halo, hydroxyl, additional aldehyde or ketone functionality, $-OC(O)R_3$, and $-C(O)R_3$ where $R_3$ is hydrogen, alkyl or alkenyl.

Preferred aldehyde or ketone reactants are aliphatic, cycloaliphatic and aromatic compounds having a boiling point above about 100° C. These compounds may be employed in the reaction without the use of solvents or elevated pressures.

The silylated trichloroacetates for use according to the instant invention are compounds of the formula

wherein $R'$ is independently phenyl or lower alkyl. The preferred silylated trichloroacetate reactant is trimethylsilyl trichloroacetate.

Silylated trichloroacetates are known compounds or they may be prepared according to known techniques such as those disclosed by T. Okada et al., *J. Organometallic Chem.*, 42, 117 (1972) or H. H. Hergott et al., *Synthesis*, 626 (1980) which teachings are herein incorporated in their entirety by reference.

The siloxy and trichloromethyl functionalized compounds formed according to the invention are those having the formula

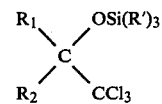

wherein $R_1$, $R_2$ and $R'$ are as previously defined.

According to the invention, the two reactants are combined at elevated temperatures in the presence of a catalytic amount of a suitable initiator. The reactants may be combined in any order. Generally temperatures from about 100° C. to about 150° C. are employed. The reaction is generally conducted at atmospheric pressures although elevated or reduced pressure may also be employed if desired. In particular, it may be found expedient as an aid to removal of silylated chloromethyl carbinol product to distill off the product under reduced pressure. In this regard it also may be advantageous to employ a sweep gas such as nitrogen or carbon dioxide in order to aid in removal of silylated trichloromethyl carbinol products.

The reactants are combined in any ratio, however, generally they are combined in about a stoichiometric ratio in order to limit the amount of unreacted starting material contaminating the desired product. Due to the fact that the silylated trichloroacetate may decompose to yield the corresponding trichloromethyl silane, particularly under basic conditions, it is advantageous to employ a slight excess of silylated trichloroacetate to allow for some loss of reactant. Preferred are ratios of aldehyde/ketone to silylated trichloroacetate of about 1:1 to about 1:2.

The reaction is initiated by the presence of one or more suitable initiators. Basic catalysts, such as alkali metal alkoxides or hydroxides, salts of strong bases and weak acids, or non-nucleophilic organic bases are all suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and ethoxides.

Additional suitable initiators include stable quaternary salts such as ammonium or phosphonium quaternary salts having inert counterions. Preferably, these salts have the general formula $(R'')_4AY$ where each $R''$ is a hydrocarbon moiety, A is a quaternary nitrogen or phosphorus atom, and Y is an unreactive neutralizing anion which may be inorganic, e.g., chloride, bromide, iodide, bicarbonate, sulfate, or the like, or Y may be an organic ion such as formate, acetate, benzoate, phenate, or bisphenate. The $R''$ groups may be alkyl, aryl, alkaryl, aralkyl, or cycloalkyl. Also, two $R''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

The quantity of initiator compound is not critical so long as any significant amount is present and available at the reaction site. Suitably from about 0.01–1 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts include the compounds generally known as phase-transfer catalysts such as, for example, cyclic polyethers and particularly oligomers of ethylene oxide known as crown ethers. Such solubilizing agents may be employed in minor amounts, for example, in the ratio of about 0.005–1.0 mole per mole of basic catalyst.

A reaction solvent is usually not required, but use of a solvent may be employed if desired. Excess silylated trichloroacetate can be used as the solvent. Relatively high boiling inert solvents such as N,N-dimethylformamide, sulfolane, dimethylsulfoxide, glycol diethers, and substituted aromatics such as anisole, o-dichlorobenzene, alkylated pyridines, and the like are also suitable.

In the usual operation of the process the reactants and initiator are combined in a reactor as previously described. Suitably the reactor is provided with a distillation head or other means to remove the volatile reaction by-products, chloroform and carbon dioxide.

The reaction proceeds rapidly and generally is completed in from about 1 to about 5 hours depending of course on the amounts of reactants, temperature and other reaction conditions. The products are recovered from the reaction vessel and separated from residual initiator compounds, if desired, by ordinary techniques such as distillation.

SPECIFIC EMBODIMENTS

Having described the invention, the following examples are provided as further illustrative and are not to be construed as limiting the invention.

EXAMPLE 1

In a glass 25 ml round-bottom flask fitted with a condenser, a mixture of 0.0125 mole of the aldehydes or ketones more particularly described in Table I, trimethylsilyl trichloroacetate (3.53 g, 0.015 mole), potassium carbonate (0.035 g, 0.25 mmole) and 18-crown-6 (0.066 g, 0.25 mmole) was warmed with stirring to about 140° C.

The reaction was monitored by nuclear magnetic resonance spectroscopy and gas-liquid chromatography. After about 2 hours reaction, the reaction was stopped and the products isolated by distillation. Purified yields are provided in Table I. All products were identified by spectroscopic and elemental analysis.

TABLE I

| Run | Ketone or Aldehyde | Product | % Yield |
|---|---|---|---|
| 1 | φ-CHO | φ-CH(CCl$_3$)OSi(CH$_3$)$_3$ | 93 |
| 2 | 2,6-dichlorophenyl-CHO | 2,6-dichlorophenyl-CH(CCl$_3$)OSi(CH$_3$)$_3$ | 82 |
| 3 | HO-C$_6$H$_4$-CHO | (CH$_3$)$_3$SiO-C$_6$H$_4$-CH(CCl$_3$)OSi(CH$_3$)$_3$ | 75 |
| 4 | CH$_2$CH$_2$CH$_2$C=O (cyclic) | CH$_2$CH$_2$CH$_2$C(CCl$_3$)OSi(CH$_3$)$_3$ (cyclic) | 96 |

TABLE I-continued

| Run | Ketone or Aldehyde | Product | % Yield |
|---|---|---|---|
| 5 | CH₂(CH₂)₃C=O (cyclic) | CH₂(CH₂)₃—C(CCl₃)OSi(CH₃)₃ (cyclic) | 90 |
| 6 | O=⟨⟩=O | 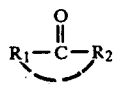 | 72 |
| 7 | CH₂(CH₂)₄C=O (cyclic) | CH₂(CH₂)₄C(CCl₃)OSi(CH₃)₃ (cyclic) | 88 |
| 8 | ⟨⟩=O | 3-trichloromethyl-3-(trimethylsiloxy)cyclohexene* | — |

*Also present were quantities of 1-(trimethylsiloxy)-3-trichloromethylcyclohexene.

What is claimed is:

1. A process for preparing siloxy and trichloromethyl functionalized compounds comprising contacting an aldehyde or ketone with a silylated trichloroacetate at elevated temperatures in the presence of an initiator.

2. A process according to claim 1 wherein the silylated trichloroacetate is trimethylsilyl trichloroacetate.

3. A process according to claim 1 wherein the aldehyde or ketone corresponds to the formula:

$$R_1-\overset{O}{\underset{\|}{C}}-R_2$$

wherein $R_1$ and $R_2$ individually are hydrogen or a hydrocarbyl radical of up to about 20 carbons selected from the group consisting of alkyl, alkenyl, aryl, and inertly functionalized derivatives thereof, provided that at least one of $R_1$ or $R_2$ is a hydrocarbyl radical; or $R_1$ and $R_2$ collectively form a hydrocarbylene moiety of up to about 20 carbons selected from the group consisting of alkylene, alkenylene and inertly functionalized derivatives thereof.

4. A process according to claim 3 wherein the inert functionality is selected from the group consisting of alkyl, aryl, alkoxy, polyalkoxy, halo, hydroxyl, additional aldehyde or ketone functionality, —OC(O)R₃ and —C(O)OR₃ where R₃ is hydrogen, alkyl or alkenyl.

5. A process according to claim 1 wherein the initiator comprises either a basic catalyst or a quaternary ammonium or phosphonium compound.

6. A process according to claim 5 wherein the basic initiator is selected from the group consisting of alkali metal alkoxides, salts of strong bases and weak acids and non-nucleophilic organic bases.

7. A process according to claim 5 wherein the initiator comprises a basic catalyst and a solubilizing agent.

8. A process according to claim 7 wherein the solubilizing agent comprises a cyclic polyether.

9. A process according to claim 1 wherein the temperature is from about 100° C. to about 150° C.

* * * * *